United States Patent [19]
Yoon

[11] Patent Number: 6,066,090
[45] Date of Patent: *May 23, 2000

[54] BRANCHED ENDOSCOPE SYSTEM

[76] Inventor: InBae Yoon, 2101 Highland Ridge Dr., Phoenix, Md. 21131

[ * ] Notice: This patent issued on a continued prosecution application filed under 37 CFR 1.53(d), and is subject to the twenty year patent term provisions of 35 U.S.C. 154(a)(2).

[21] Appl. No.: 09/099,792

[22] Filed: Jun. 18, 1998

Related U.S. Application Data

[60] Provisional application No. 60/050,180, Jun. 19, 1997.

[51] Int. Cl.⁷ ..................................................... A61B 1/005
[52] U.S. Cl. ........................... 600/113; 600/146; 600/173
[58] Field of Search .................................... 600/102, 109, 600/113, 111, 166, 160, 146, 173; 348/72, 45

[56] References Cited

U.S. PATENT DOCUMENTS

| | | | |
|---|---|---|---|
| 5,166,787 | 11/1992 | Irion | 348/45 |
| 5,178,130 | 1/1993 | Kaiya | 600/113 |
| 5,196,928 | 3/1993 | Karasawa et al. | 600/113 |
| 5,305,121 | 4/1994 | Moll | 348/45 |
| 5,368,015 | 11/1994 | Wilk | 600/166 |
| 5,653,677 | 8/1997 | Okada et al. | 600/111 |
| 5,817,015 | 10/1998 | Adair | 600/121 |

FOREIGN PATENT DOCUMENTS 5115425   5/1993   Japan .

*Primary Examiner*—John P. Leubecker
*Attorney, Agent, or Firm*—Blank Rome Comisky & McCauley LLP

[57] ABSTRACT

An endoscope has two or more branches and each branch may include a source of illumination and a lens train, fiber optic bundle, or solid state image receiving device. Each branch end is independently manipulable or steerable and thus produces an image from a distinct point of view within the body (e.g., front and side views); the images are juxtaposed on a video monitor for simultaneous viewing by the surgeon. Each branch also includes an operating channel or cannula through which various surgical instruments are passed. A first branch may be used to pass an instrument to the situs of a surgical procedure and a second branch may be used to view that situs from a second, separate point of view. Additionally, the second branch may be used to introduce a second surgical instrument through the second branch cannula to approach the situs of the procedure from the angle of the second branch.

16 Claims, 5 Drawing Sheets

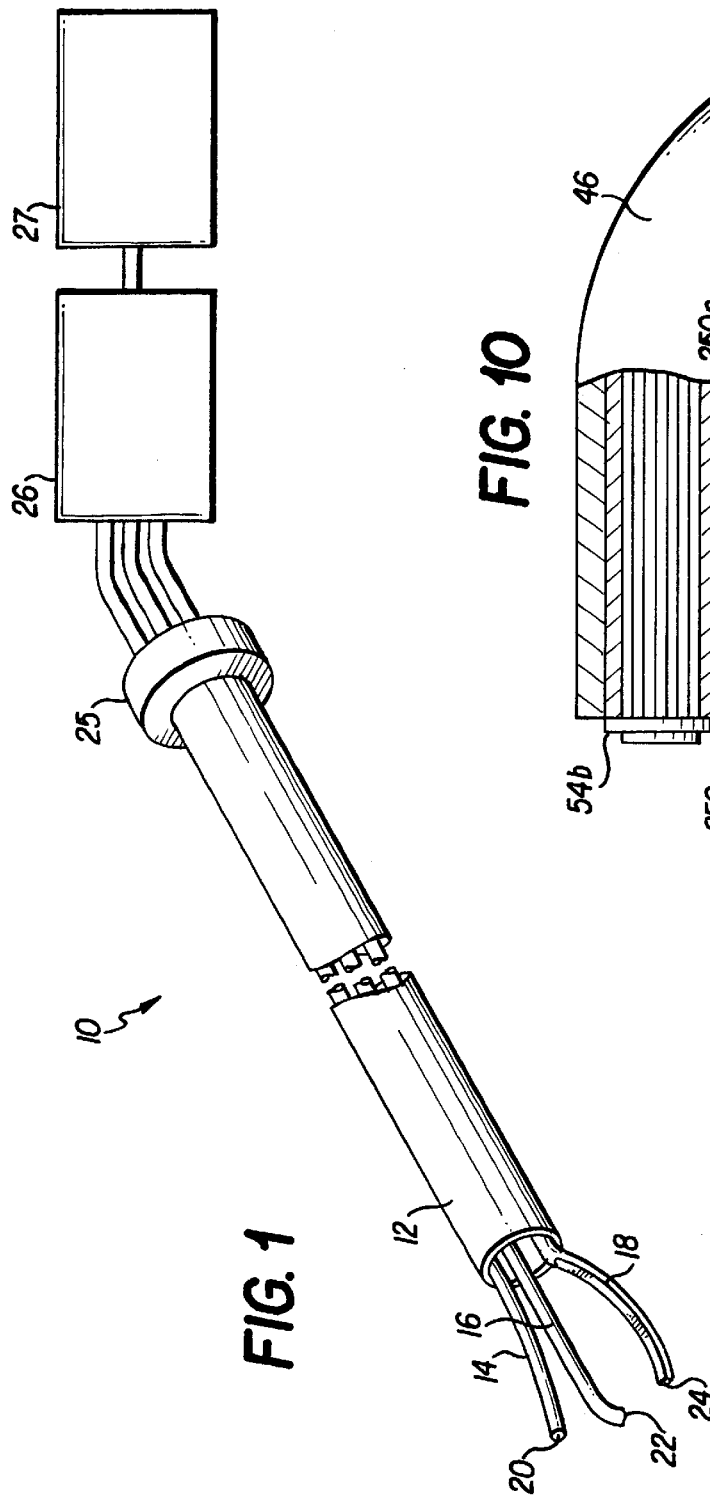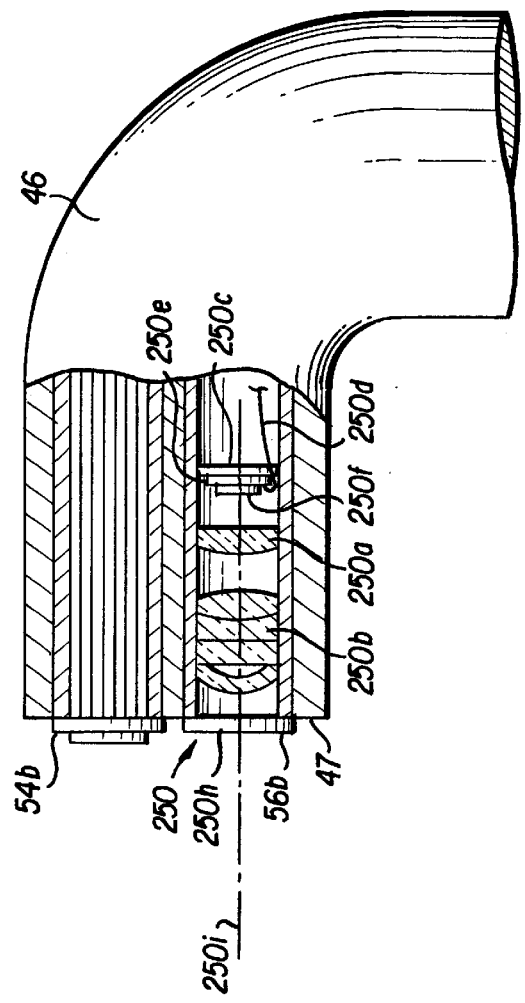

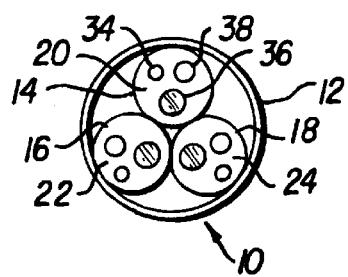
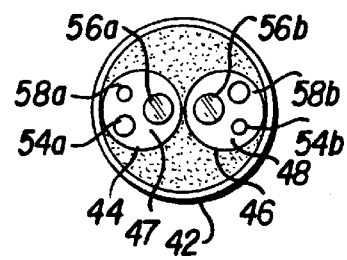
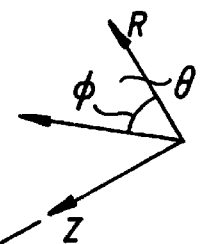
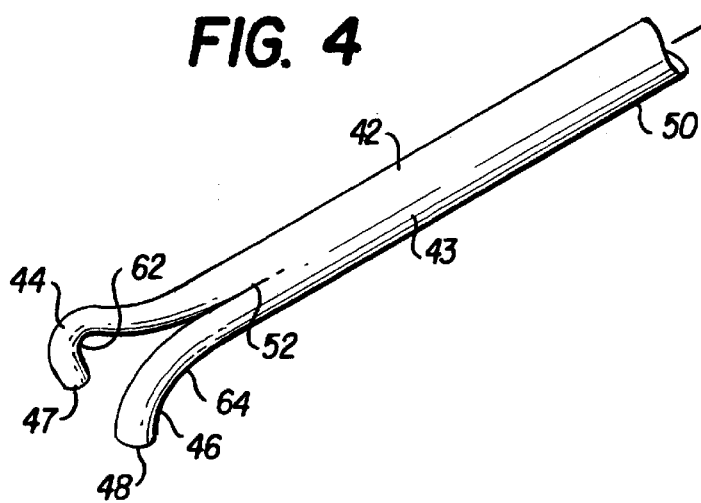
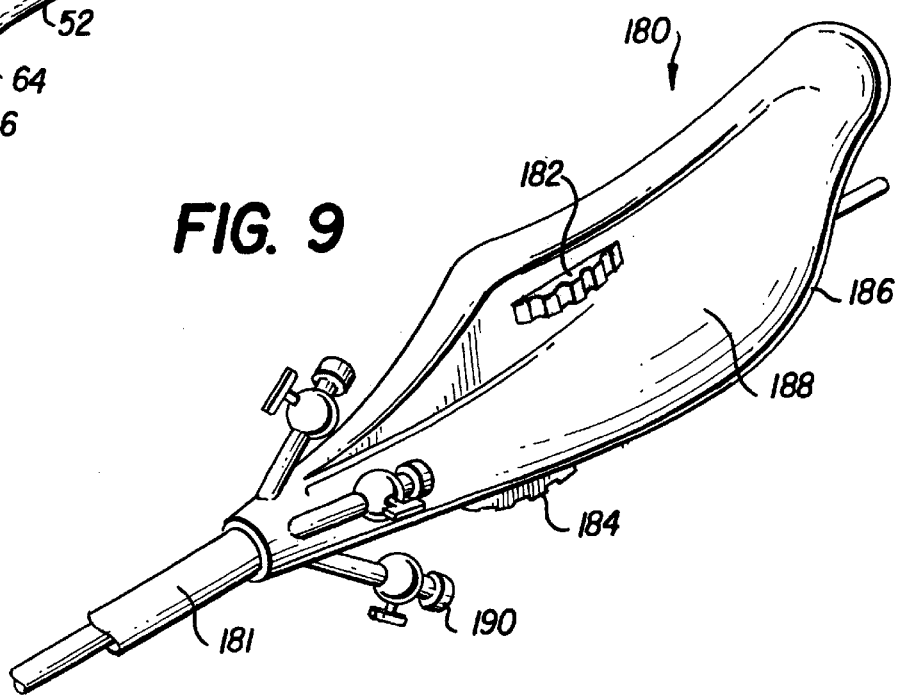

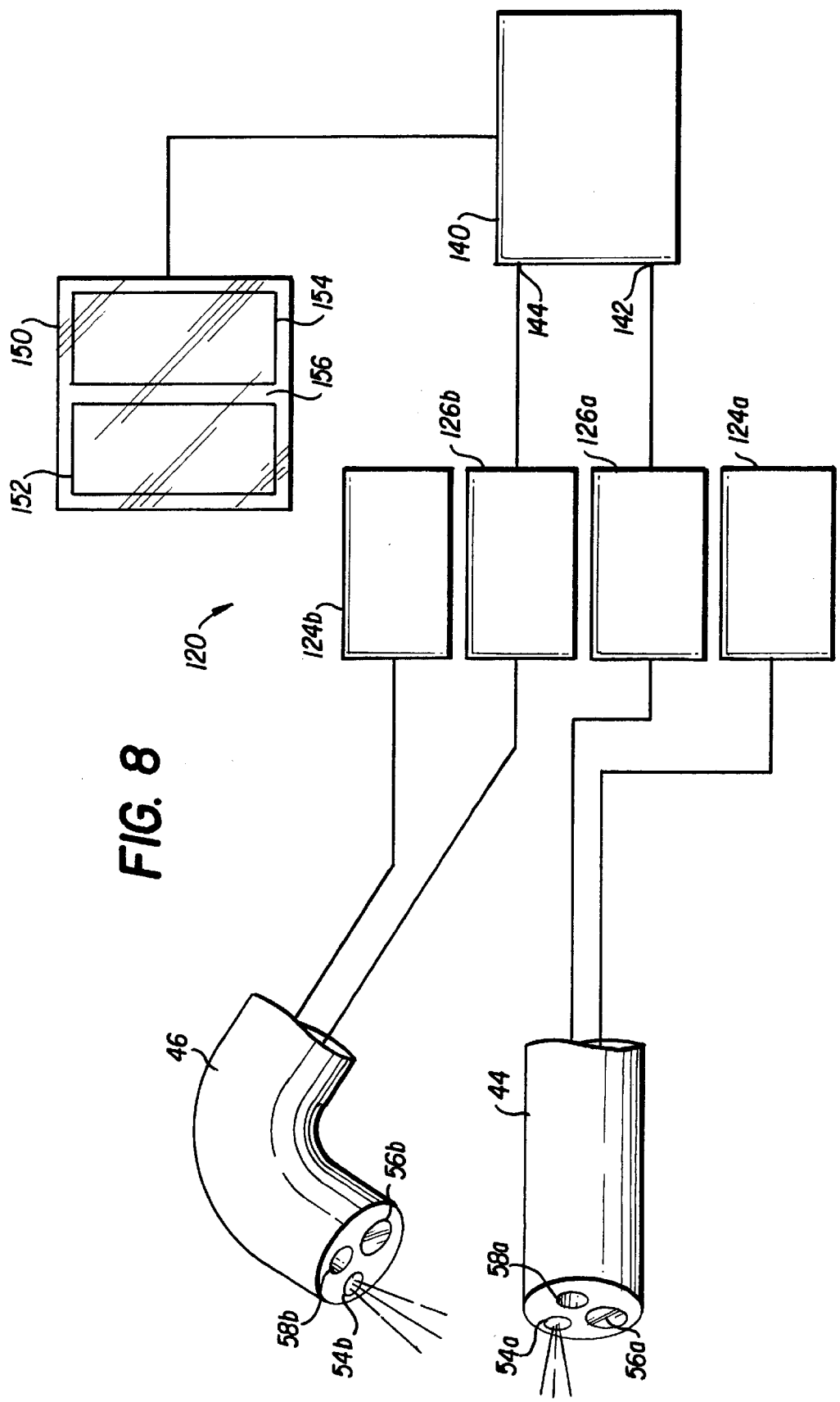

BRANCHED ENDOSCOPE SYSTEM

BACKGROUND OF THE INVENTION

This application claims benefit of provisional application No. 60/050,180, filed Jun. 19, 1997. This application is also related to Applicant's application filed concurrently herewith entitled "Biopsy and Lumpectomy Instrument and Method for Using the Same", the entire disclosure of which is incorporated herein by reference.

FIELD OF THE INVENTION

The present invention relates to endoscopic instruments for viewing of surgical procedures and organ structures inside the body.

DISCUSSION OF THE PRIOR ART

Recently, there have been dramatic advances in the field of endoscopic instrumentation and in the application of endoscopic techniques to a growing number of surgical procedures. A number of benefits are thus realized, including reduced pain and discomfort, shortened recovery time and better cosmetic results; endoscopic surgery will, therefore, continue to be a widely applied technique and an area of continuing development.

Endoscopic surgery is performed with hollow, tubular, elongated instruments inserted through small incisions in the skin, and is viewed through an endoscope. The endoscope is an optical instrument typically incorporating at least one source of light to provide illumination within the body and a lens, fiber optic bundle or image sensing device for transmitting the image from the surgical site within the body to an eyepiece or display outside the body. The surgeon performing an endoscopic surgical procedure cannot directly see, grasp and manipulate organ structures in the body as with open surgery, so it is important to provide endoscopic instruments that are convenient to use and viewing systems that convey as much information as possible.

Traditionally, endoscopes utilize a single objective lens with a lens train fiber optic bundle and so only provide a single view of a given surgical procedure, where that single view is necessarily from a single point of view or perspective. The single view provides a two-dimensional image and provides no opportunity for a simultaneous second perspective; thus, it is impossible to see what is behind or next to the object in front of the endoscope distal end.

Stereoscopy has been employed in an effort to provide a simulated three-dimensional image to the surgeon, however, even stereoscopic endoscopes show a view of a surgical situs from a single binocular perspective and so provide no information on what lies behind or next to the object in front of the endoscope distal end. Additionally, use of stereoscopic endoscopes customarily require the surgeon to don an awkward stereoscopic display or viewer on the face, over the eyes.

An endoscope usually has a tubular body and may include an operating channel or cannula for insertion of surgical instruments such as those used in making incisions or performing other surgical steps. A surgeon using the prior art endoscope is relegated to a straight-on view of the object (e.g., an organ structure being incised) and the view may be occluded by the use of opaque endoscopic instruments. Accordingly, there is a need for an apparatus or method allowing the surgeon to view the surgical site from a second perspective or angle, in addition to that provided by the single viewing element of the prior art.

OBJECTS AND SUMMARY OF THE INVENTION

It is a primary object of the present invention to overcome the above-mentioned disadvantages of the prior art by providing an endoscope system including an endoscope having multiple branches and a viewing monitor or display capable of simultaneously displaying one or more of the images from the endoscope branches in any selected position on the monitor screen.

A further object of the present invention is to provide a branched endoscope system permitting the surgeon to view a first endoscope branch distal end from the perspective of a second endoscope branch distal end manipulated or aimed to view the first branch distal end from a perspective substantially transverse to the axis of the first endoscope branch.

Yet another object of the present invention is to provide a branched endoscope system permitting a surgeon to insert a first endoscope branch into a hollow organ structure through an incision in an organ wall while a second endoscope branch visualizes the organ wall externally during the incision and insertion steps.

In accordance with the present invention, an endoscope has two or more endoscope branches; each endoscope branch preferably has a flexible shaft including a source of illumination and a lens train, fiber optic bundle, CCD solid state image sensor or CMOS solid state image sensor. Each endoscope branch end is separately and independently manipulable or steerable and generates an image of an object within the body from a distinct point of view (e.g., front and side views). The images may be juxtaposed on a video monitor or display for simultaneous viewing.

Advantageously, each endoscope branch may also include an operating channel or cannula through which various surgical instruments or fluids may be passed. A first endoscope branch cannula may be used to pass an instrument to the site of a surgical procedure and a second endoscope branch may be used to view the surgical site from a second, separate point of view. Additionally, the second endoscope branch cannula may be used to introduce a second surgical instrument to approach the surgical site from the angle of the second branch, such that two surgical instruments are brought to bear on the surgical site and each endoscope provides a distinct point of view; both points of view are presented simultaneously on the monitor, thereby making it easier for the surgeon to discern the position and orientation of the surgical instruments.

In another method, a first endoscope branch is inserted into a hollow organ structure through an incision in the organ structure wall while a second endoscope branch visualizes the organ wall incision externally, thereby permitting the surgeon to simultaneously view the insertion of the first endoscope branch end from the perspective of the first and second endoscope branch ends.

As noted above, each endoscope branch end has a shaft adapted to be inserted through a portal and into the body; by "portal" is meant either incised or natural openings in the body. The branched endoscope branches are initially aligned in a straight, parallel and juxtaposed configuration to facilitate insertion of the branched endoscope branches into the body.

In one embodiment, an endoscope branch includes a solid state complementary metal oxide semiconductor (CMOS) image sensor carried on the branch distal end. CMOS image sensors are fabricated using the economical CMOS process, an Integrated Circuit (IC) fabrication technology combining enhancement mode N-channel (NMOS) and enhancement mode P-channel (PMOS) Field Effect Transistors (FETs) on a single substrate to form logic gates, memory cells, or other devices. CMOS image sensors are readily fabricated on a single substrate (or chip) incorporating image sensing pixels and the required image signal processing circuitry for converting periodically sampled pixel voltage levels into an image display ready signal adapted for display on, preferably, a color image display. Examples of general purpose CMOS image sensors include U.S. Pat. No. 5,225,696 (to Bahraman) disclosing an image sensor with MOS photodetectors, U.S. Pat. No. 5,461,425 (to Fowler et al.) disclosing a CMOS image sensor with pixel level A/D conversion on a single chip 10, U.S. Pat. No. 5,614,744 (to Merrill.) disclosing a CMOS image sensor with active pixels incorporating anti-blooming isolation guard rings, U.S. Pat. No. 5,665,959 (to Fossum et al.) disclosing a CMOS image sensor with a focal-plane digital photon-counting array, and U.S. Pat. No. 5,708,263 (to Wong) disclosing a CMOS image sensor photodetector array with a simplified pixel circuit allowing denser arrays of pixels to be fabricated onto a chip; the entire disclosures of each reference identified above are incorporated herein by reference.

In the branched endoscope system of the present invention, the CMOS image sensor is integrated onto a substrate or chip, preferably incorporated into a sealed optics package including one or more objective lens elements (disposed along an optical axis) and a printed circuit board or substrate carrying electrical connections proximally from the CMOS image sensor. The sealed optics package is incorporated into the distal end of the endoscope branch. The endoscope branch may be steered or aimed to provide a desired field of view of a surgical procedure or an object in the body; steering or aim is preferably controllable from the branched endoscope instrument proximal end using control members (e.g., tethers or wires) connected to handle-mounted control wheels (as disclosed in FIG. 19 of Applicant's U.S. Pat. No. 5,437,680, the entire disclosure of which is incorporated herein by reference).

In an alternative embodiment, the endoscope branch has a fixed objective lens carried on the distal end of an endoscope branch and a lens train or fiberoptic bundle transmits the endoscopic image proximally to a CMOS sensor located in a proximal housing or hand piece.

The CMOS pixel signal processing circuitry converts image light energy into image ready signal energy adapted for transmission out of the body through connecting wires or, optionally, over an RF, microwave, or acoustic data link to a receiver connected to an image display.

The foregoing and additional objects, features and advantages of the invention will become apparent to those of skill in the art from the following detailed description of a preferred embodiment, taken with the accompanying drawings, wherein like reference numerals in the various drawings identify like components.

BRIEF DESCRIPTION OF THE DRAWINGS

FIG. 1 is a schematic illustration of the branched endoscope system of the present invention including a perspective view of a branched endoscope.

FIG. 2 is an end view of the branched endoscope of FIG. 1.

FIG. 3 is an end view of an alternative embodiment of the branched endoscope.

FIG. 4 is a perspective view of the branched endoscope of FIG. 3.

FIG. 8 is a schematic illustration of a branched endoscope system including the branched endoscope ends of FIGS. 3 and 4.

FIG. 9 is a perspective illustration of a branched endoscope proximal end or hand piece.

FIG. 10 is a partial cross section of a branched endoscope distal end incorporating a solid state CMOS image sensor.

DESCRIPTION OF THE PREFERRED EMBODIMENT

Figure 5:
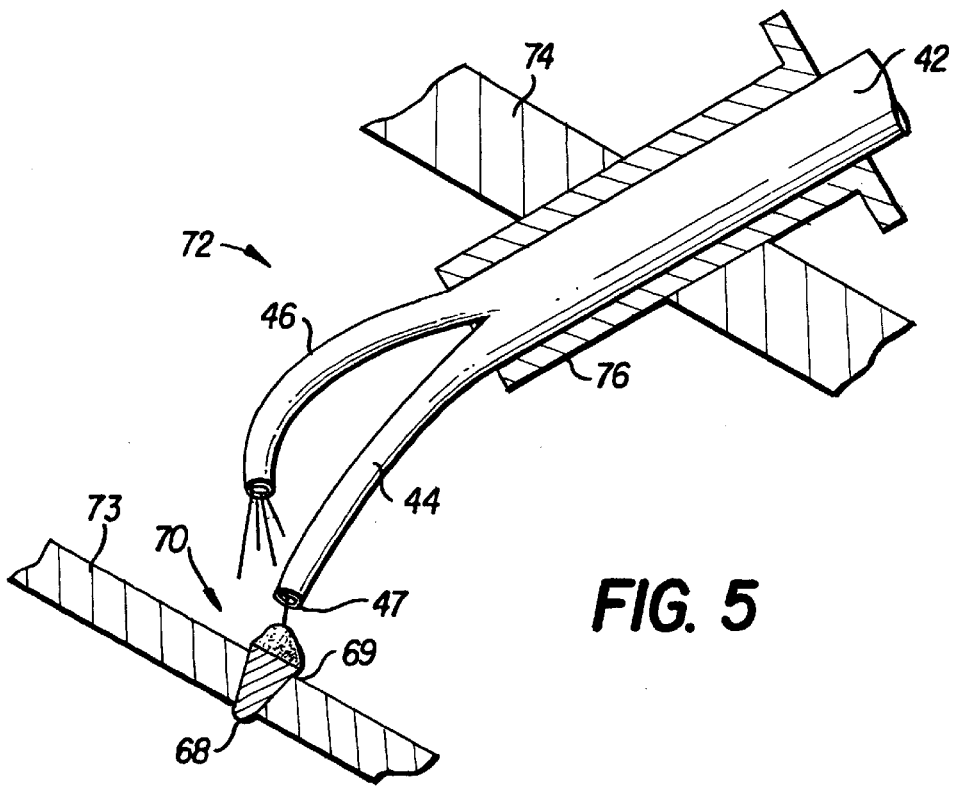
FIG. 5 is a perspective illustration in partial section of the branched endoscope in use inside the body.

Referring specifically to FIG. 1 of the accompanying drawings, there is illustrated a branched endoscope system 10 including a rigid or flexible tubular main trunk or endoscope body 12 having a longitudinal axis, a proximal open end 25 opposite a distal open end and a lumen or channel therebetween. Endoscope body 12 is adapted for insertion through a portal into the body. Endoscope system 10 preferably includes a first elongate, flexible endoscope branch 14, a second elongate, flexible endoscope branch 16 and a third elongate, flexible endoscope branch 18. The first, second and third endoscope branches 14, 16 and 18, are each rotatable about their respective longitudinal axes and project distally from tubular body 12. First endoscope branch 14 has a steerable distal end 20; similarly, second endoscope branch 16 has a steerable distal end 22 and third endoscope branch 18 has a steerable distal end 24. The endoscope branch distal ends 20, 22 and 24 are separately and individually steered or manipulated using controls adjustable from the proximal end 25 of endoscope body 12, as is well known in the art. Endoscope body proximal end 25 is illustrated schematically in FIG. 1 and may carry any suitable hand piece including the steering controls as shown, for example, in FIG. 19 of Applicant's U.S. Pat. No. 5,437,680, the entire disclosure of which is incorporated herein by reference). Preferably, a separate steering control mechanism is included for steering each endoscope branch; the orientation and actuation of the steering controls for the endoscope branches is illustrated in further detail below.

The endoscope branches 14,16 and 18 are initially straight, juxtaposed and aligned in a parallel array (as shown in the end view of FIG. 2) for easy insertion into a portal sleeve (not shown), or other portal into the body. Each endoscope branch may be steered, after insertion through the portal, to assume any of various configurations as exemplified in FIG. 1, in which first endoscope branch 14 curves away from the central axis of endoscope body 12 while second endoscope branch 16 curves sharpy proximate distal end 22 to provide a transverse view of third endoscope branch distal end 24.

Each endoscope branch 14,16, and 18 includes an image sensor generating image signals for input to a processor 26. Processor 26 provides display signals to an image display monitor 27 for display of images from the endoscope branches.

Turning back to FIG. 2, an axial end view of the distal end of branched endoscope system 10 shows the outer circumference of the endoscope body 12, the first endoscope branch distal end 20, the second endoscope distal end 22 and the third endoscope branch distal end 24. Each endoscope branch distal end preferably includes an illumination source 34, an image receiver 36 and an operating channel or cannula 38. The illumination source distally projects light generated by a light emitting diode (LED), an incandescent lamp or another source of illumination, as is well known in the art. Preferably, a lamp or light generator is contained within a hand piece or housing at the proximal end of endoscope body 12 and the light is transmitted distally to the illumination source 34 on an endoscope branch distal end via a lens train, optical waveguide, fiber optics, or the like. In an alternative embodiment, the lamp is situated proximate the distal end of the endoscope branch.

The endoscope branch image receiver 36 may include a train of lenses leading back to an image sensor or transducer disposed at the proximal end 25 of the endoscope body 12. Alternatively, the image receiver may include an optical waveguide or fiber optic bundle for transmitting the image from the distal end of the endoscope branch (e.g., 20, 22 or 24) to an image transducer at the proximal end of endoscope body 12. Alternatively, a solid state image sensor or transducer such as a charge coupled device (CCD) image sensor or a CMOS image sensor may be located proximate the distal end of an endoscope branch; a distally mounted image sensor transmits an image signal to the proximal end of endoscope body 12, preferably via an electrical connection. An embodiment including a CMOS image sensor is described in greater detail below.

Turning now to FIGS. 3 and 4, a two-branch endoscope 42 includes a first endoscope branch 44 and a second endoscope branch 46; each branch is separately steerable and first endoscope branch 44 may be used to view the distal end 48 of second endoscope branch 46, as shown in FIG. 4.

The endoscope branches 44 and 46 are initially straight, juxtaposed and aligned in a parallel array (as shown in the end view of FIG. 3) for easy insertion into a portal sleeve (not shown), or other portal into the body. Each endoscope branch may be steered, after insertion through the portal, to assume any of various configurations as exemplified in FIG. 4. The tubular body or main trunk of two branch endoscope 42 preferably has a circular cross-section at the midpoint 50, as can be seen from the distal end view of FIG. 3, and tapers gradually from a circular cross-section at midpoint 50 to a figure eight cross-section at the branching point 52. The endoscope branches 44, 46 are preferably substantially circular at the branch distal ends 47, 48. As above, endoscope branch 44 includes an illumination source 54a, an image receiver 56a and an operating channel or cannula 58a; similarly, endoscope branch 46 includes an illumination source 54b, an image receiver 56b and an operating channel or cannula 58b.

As illustrated in FIG. 4, each endoscope branch 44, 46 is separately steerable, (i.e., manipulable or controllable) for position and angular orientation. For example, the distal end 47 of first endoscope branch 44 can be contracted or curled inwardly toward the longitudinal axis 60 of endoscope body 43, as illustrated in FIG. 4 and can assume any transverse angular orientation, meaning that the distal end 47 may be aimed transversely away from the central longitudinal axis 60 at any angular orientation and in any direction. Each branch 44, 46 is selectably steerable through an angular sweep of 360 degrees with respect to the endoscope central longitudinal axis 60 (lying along the Z axis of the coordinate system, as shown in FIG. 4). Thus, each endoscope branch 44, 46 is independently steerable to extend linearly and perpendicularly from the branching point 52 in the radial direction, R, and may be adjusted at any selected angle φ. Each endoscope branch 44, 46 may also be independently adjusted to a range of angles θ for a selectable sweep of azimuth and may be steered to assume a small radius curl 62 as shown for first endoscope branch 44, or may be steered in a large radius curl 64 as is illustrated for second endoscope branch 46 in FIG. 4. Suitable endoscope steering control mechanisms are available; for example, U.S. Pat. No. 4,982,725 to Hibino et al. discloses a controller and bendable endoscope elongate part, and U.S. Pat. No. 5,168,864 to Shockey discloses a deflectable or steerable endoscope having an elongate body curveable in a selectable radius; the entire disclosures of which are incorporated herein by reference.

By independently steerable endoscope branches is meant steerable and adjustable without altering the position of other branches. Thus, for example, first endoscope branch 44 is steered to a selected spatial orientation without altering the spatial orientation of second endoscope branch 46. This is to be distinguished from simultaneous or synchronous adjustments, as required for stereoscopic endoscope use. The branched endoscope system of the present invention can include two, three or more endoscope branches and individual endoscope branches can be rotatable about their respective longitudinal axes. Individual endoscope branches can be flexible and steerable (as described above) or rigid; alternatively, an individual endoscope branch may be rigid for a portion of the longitudinal length of the branch tubular body and flexible and steerable for the remaining length. Alternatively, a side endoscope branch can projecting distally at an angle from a mid-point of the tubular body side of a main endoscope branch; the side endoscope branch is then rotatable about the longitudinal axis of the main branch which can support and second side branch and a third side branch, each of which project distally at an angle from a different location on the main branch side wall.

In use, e.g., as in laparoscopic surgery, illustrated in FIG. 5, an internal body cavity 72 is pressurized with gas to distend the abdominal wall 74, after the abdominal wall has been pierced with a trocar (not shown) or other penetrating member. The two branch endoscope 42 is introduced into the body via a hollow tube or portal sleeve 76 inserted through the abdominal wall 74 (note that, in FIGS. 5 and 6, the branch distal ends 47, 48 are represented schematically; please refer to FIG. 3 for a detailed view of the branch distal ends 47, 48). First endoscope branch 44 and second endoscope branch 46 are individually steered or adjusted to provide simultaneous views of a selected object or region in the body.

First endoscope branch 44 provides a first view of a surgical site 70; second branch 46 is steerable to permit illumination and viewing of the surgical site 70 from a second perspective. In the example of FIG. 5, an expandable plug member 68 is inserted into an opening 69 in an organ structure or wall 73 and a balloon 71 carried on a catheter and within expandable plug member 68 is expanded, thus expanding plug member 68 to fill or occlude organ structure opening 69. Second endoscope branch 46 provides a substantially transverse or side-long view of the distal end 47 of branch 44 and of the surgical site 70.

The method for an exemplary procedure illustrated in FIG. 5 includes the steps of illuminating and viewing a surgical site 70 with a first endoscope branch 44, illuminating and viewing a surgical site 70 with a second endoscope branch 46, introducing a surgical instrument to make an incision at surgical site while simultaneously viewing the incision from one or both of the surgical endoscope branches 44,46, introducing a second surgical instrument (e.g., a catheter carrying plug 68) through a branch cannula while simultaneously viewing the surgical site (or the second surgical instrument) from one or both of the surgical endoscope branches 44, 46.

Figure 6:
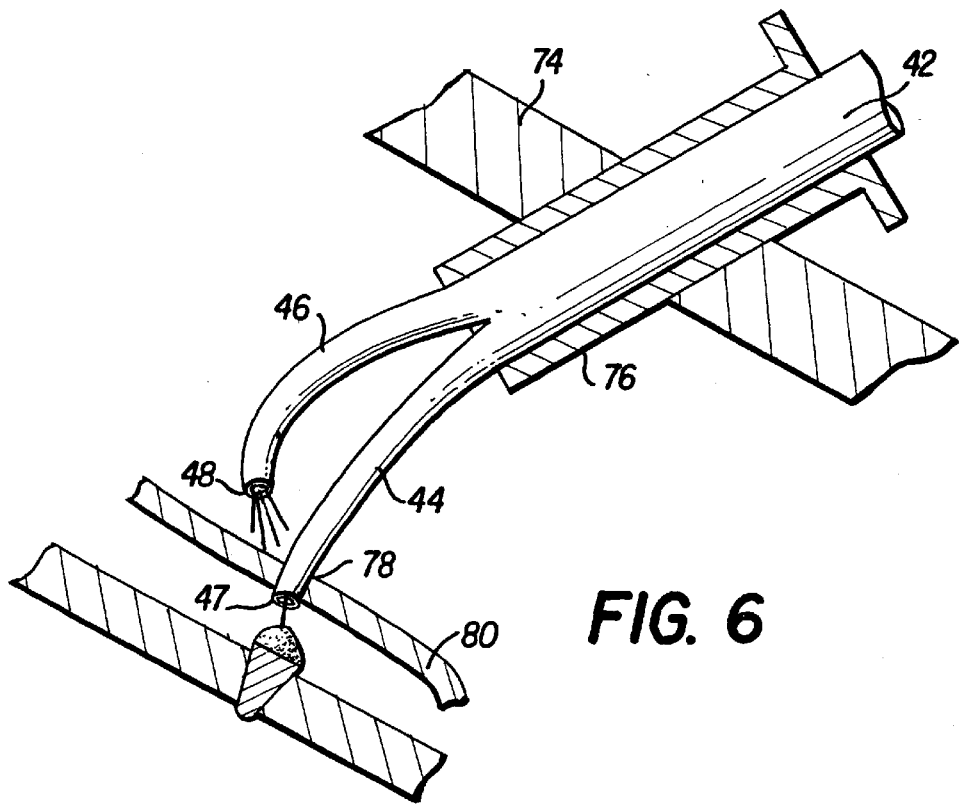
FIG. 6 is a perspective illustration in partial section of the branched endoscope inside the body.

FIG. 6 illustrates another method of the present invention in which branched endoscope 42 is inserted into the body through a portal sleeve 76 and an incision 78 is made in an organ wall 80, preferably using an cuffing instrument (not shown) inserted in the operating channel or cannula 58*a* of first branch 44, while viewing the site of the incision 78 in organ wall 80 from either or both of first endoscope branch distal end 48 and second endoscope branch 47. First endoscope branch distal end 47 is then inserted through incision 78. Thus, first branch 44 is inserted into a hollow organ structure through incision 78 in the organ structure wall 80 while second branch 46 visualizes the organ wall incision 78 externally, thereby permitting the surgeon to simultaneously view the insertion of the first branch end 47 from the perspectives of the first endoscope branch distal end 47 and second endoscope branch distal end 48.

Figure 7:
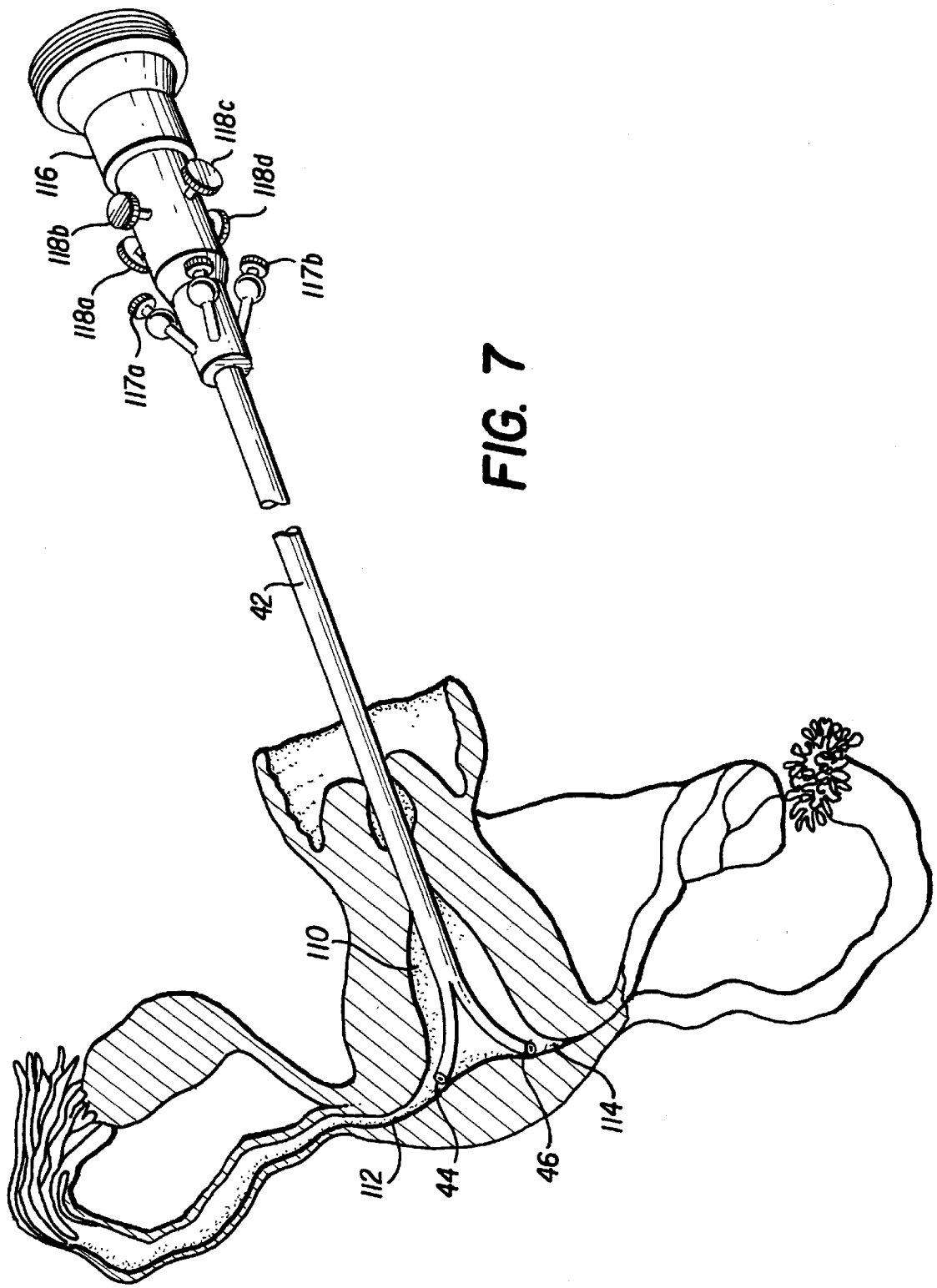
FIG. 7 is a perspective illustration of the branched endoscope in use inside the body.

As illustrated in FIG. 7, a branched endoscope is readily used in viewing and performing simultaneous procedures at separate surgical sites. In the illustrated example, a branched endoscope 42 can be inserted vaginally into the uterus 110 wherein first branch 44 and second branch 46 are steered toward first and second utero-tubal junctions (UTJs) 112, 114, respectively, for simultaneous visualization of the UTJs 112, 114 and insertion of contraceptive devices such as expandable plugs, or the like. Branched endoscope 42 includes a proximal hand piece 116 carrying at least two proximally mounted angled ports 117*a*, 117*b*, each including a stopcock and luer lock for attachment to tubing used in passing fluids for irrigation or aspiration or for introduction of surgical instruments, as described above. Each endoscope branch operating channel or cannula (e.g., 58*a*) is in fluid communication with and terminates distally in an angled port (e.g., 117*a*). Hand piece 116 also includes steering controls 118*a*–118*d* including a plurality of knobs connected through a tether tension controlling mechanism for controlling steering of the of the individual endoscope branches 44, 46. In the embodiment of FIG. 7, control knob 118*a* moves endoscope branch 44 in an arc lying in a first plane defined as up and down, control knob 118*b* moves endoscope branch 44 in an arc lying in a second plane transverse to the first plane and defined as left and right; similarly, control knob 118*c* moves endoscope branch 46 in an arc lying in a first plane defined as up and down, and control knob 118*d* moves endoscope branch 44 in an arc lying in a transverse, second plane defined as left and right. A collapsed expandable plug to be inserted in UTJ 112 is disposed over a collapsed balloon catheter (not shown) and the catheter is inserted into proximal port 117*a* and advanced distally to project out of operating channel 58*a* while the surgeon views the UTJ 112 with first endoscope branch 44. Simultaneously, the surgeon can view and perform any needed surgical procedure at the second UTJ 114 using second endoscope branch 46.

The branched endoscope system of the present invention can also be used in performing the Biopsy and Lumpectomy procedure described in applicant's copending patent application entitled "Biopsy and Lumpectomy Instrument and Method for Using the Same", filed concurrently herewith, said application is incorporated herein in its entirety by reference.

FIG. 8 is a schematic illustration of a branched endoscope system 120 including first and second branches 44, 46, as above, each connected to respective illumination subsystems 124*a*, 124*b* and image processing subsystems 126*a*, 126*b*. The illumination subsystems 124*a*, 124*b* each include circuitry to power and control the light generators connected to the illumination sources (e.g., 54*a* in endoscope branch 44 and 54*b* in endoscope branch 46) providing distally projecting illumination covering substantially the entire field of view of the corresponding endoscope branch image receiver 56*a*, 56*b*. Each image processing subsystem (e.g., 126*a*) includes circuitry to power, control and an receive an unprocessed image signal input from the corresponding image receiver (e.g., 56*a*). The image processing subsystems 126*a*, 126*b* provide a processed image signal to a display image processor 140 via a first input connection 142 and a second input connection 144, respectively. Display image processor 140 provides control of the video or image signals from the image receivers of first branch 44 and second branch 46, including selecting whether a video image signal from first input 142 or second input 144 is to be displayed and the position of the displayed image on the video monitor 150. Images from any endoscope branch may be selected for display on monitor 150. Monitor 150 is connected to and receives image display ready (or processed) signals from display image processor 140 and is capable of simultaneous display of a first image 152 from first input 142 and a second image 154 from second input 144, in any selected position on the video monitor screen 156; the positions of displayed images on the monitor screen 156 are controllable using display image processor 140.

A second embodiment of a branched endoscope proximal end or hand piece 180 is illustrated in FIG. 9, and includes first steering control wheel 182 and second steering control thumb wheel 184 for steering endoscope branch ends through respective control mechanisms, as discussed above. Hand piece 180 is carried on the proximal end of an endoscope tubular body 181 terminated distally in two or more endoscope branches. The hand piece includes a sculpted grip 186 with a palm swell 188 and is comfortably grasped and manipulated by the surgeon. Hand piece 180 also preferably includes at least one angled port 190 for each branch cannula.

Turning now to FIG. 10, endoscope branch 46 is schematically illustrated in partial cross section, taken along a plane parallel to the longitudinal axis of the tubular body of branch 46 and bisecting image receiver 56*b* and illumination source 54*b*. In the embodiment of FIG. 10, image receiver 56*b* is a solid-state CMOS image sensor 250 and illumination source 54*b* includes a bundle of fiberoptic waveguide elements 200 transmitting illumination distally from a light generator preferably disposed within and carried by a proximal hand piece (e.g. 116).

A CMOS image sensor 250 includes a plurality of pixels (e.g., in a rectangular grid, 640 pixels by 480 pixels) and is affixed to and carried by endoscope branch distal end 47. The CMOS image sensor is integrated onto a substantially planar chip 250*e*, preferably incorporated into a sealed optics package 250*a* including one or more objective lens elements 250*b* and a printed circuit board or substrate 250*c* carrying electrical connections between electrical conductors or wires 250*d* and the CMOS image sensor chip 250*e*; the sealed optics package 250*a* is mounted onto or integrated in the branch distal end 47, preferably proximate the illumination source 54*b*.

By CMOS image sensor is meant a solid-state image sensor fabricated using the well known, economical, complementary metal oxide semiconductor (CMOS) process, i.e., the Integrated Circuit (IC) fabrication technology usually combining either or both of enhancement mode N-channel (NMOS) and enhancement mode P-channel (PMOS) Field Effect Transistors (FETs), preferably on a single substrate to form logic gates, memory cells, or image sensor pixels. CMOS image sensors preferably incorporate, on a single substrate (or chip), image signal processing, memory, and data transmission CMOS circuitry to generate image display ready signals and transfer the image display ready signals proximally out of the body for recording or display. By image display ready signal is meant a signal processed and adapted to be readily displayed on an image display such as video monitor 150. Any of several standards for image signal processing and transmission are suitable; for example, signal processing circuits on chip 250e can convert periodically sampled individual pixel voltage (or current) levels into a National Television System Committee (NTSC) image signal for transmission out of the body and display on an NTSC compatible image display (e.g., video monitor 150).

The CMOS image sensor 250 preferably has a plurality of MOS pixel circuits integrated onto chip 250e proximate a Red-Green-Blue (RGB) mosaic color filter panel 250f (as shown in FIG. 3) constituted by a mosaic arrangement of red, green, and blue color filters, thus permitting any single pixel to receive either red, green or blue filtered light energy. The color mosaic filter panel 250f is disposed on the optical axis 250i of optics package 250a, ahead of the transverse imaging surface of the CMOS chip 250e. The pixels receiving red, green, and blue light generate, respectively, red, green, and blue pixel light intensity values, for color image ready signal generation. The lens elements 250b comprising the objective lens in sealed optics package 250a are preferably fixed in position providing a fixed depth of field at an image plane substantially coincident with a plane containing the pixels of CMOS image sensing chip 250e. The optical axis 250i (shown as a dotted line through sealed optics package 250a in FIG.10) extends linearly from the image light transmissive, sealed protective cover or window 250h mounted on branch distal end 47, proximally to image sensing chip 250e being disposed transverse thereto, in the image plane. The objective lens comprised of lens elements 250b focuses an image corresponding to the endoscope branch field of view at the image plane intersecting and transverse to optical axis 250i. The objective lens is preferably fixed focus, meaning that a fixed depth of field is provided having a selected minimum in-focus distance (i.e., a minimum distance from the objective lens elements for which an observed object will remain in focus) and so objective lens elements 250b define a focal plane coincident with the image plane of image sensor chip 250e.

Optionally, the objective lens elements 250b may be individually movable for adjustable focus, preferably using a motorized focus control mechanism and may also provide variable magnification (i.e., zoom).

In the preferred embodiment, however, the lens elements are fixed in position to provide an in-focus image at all distances from the branch distal end 47 greater than selected minimum in-focus distance. Fixed focus optics are preferred for disposable embodiments due to economy of manufacture.

In an alternative embodiment, the endoscope branch has a fixed objective lens carried on the distal end of an endoscope branch and a lens train or fiberoptic bundle transmits the endoscopic image proximally to a CMOS sensor located in a proximal housing or hand piece. The CMOS pixel signal processing circuitry converts image light energy into image ready signal energy adapted for transmission out of the body through connecting wires or, optionally, over an RF, microwave, or acoustic data link to a receiver connected to an image display.

Having described preferred embodiments of a new and improved branched endoscope system, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A branched endoscope system for providing a view of the surgical cavity, comprising:
    a first endoscope branch steering control mechanism;
    a second endoscope branch steering control mechanism;
    a first endoscope branch having a steerable distal end and including a first image receiver generating a first image signal, said steerable distal end of said first endoscope branch being responsive to said first endoscope branch steering control mechanism by moving to a desired orientation;
    a second endoscope branch having a steerable distal end and including a second image receiver generating a second image signal, said steerable distal end of said second endoscope branch being responsive to said second endoscope branch steering control mechanism by moving to a desired configuration; and
    said second endoscope branch steering control mechanism and said first endoscope branch steering control mechanism being operable independently of one another resulting in independent movement of the steerable distal ends of the first and second endoscone branches while the first and second endoscope branches being sized and adapted for insertion into the surgical cavity through a single portal.

2. The branched endoscope system of claim 1, further comprising:
    an image processor responsive to said first and second image signals and generating therefrom a first image display signal and a second image display signal;
    a display responsive to said first image display signal and to said second image display signal, said display providing display of an image corresponding to a selected one of said first image display signal and said second image display signal.

3. The branched endoscope system of claim 2, wherein said display provides simultaneous display of a first image corresponding to said first image display signal and a second image corresponding to said second image display signal.

4. The branched endoscope system of claim 1 wherein said first endoscope branch further includes a light source.

5. The endoscope of claim 1 wherein said first endoscope branch further includes a cannula.

6. The branched endoscope system of claim 1, wherein said first image receiver comprises:
    a) a substantially planar complementary metal oxide semiconductor (CMOS) image sensor including a plurality of pixels and a pixel signal processing circuit generating an image ready signal, converting image light energy into electrical image display ready signal energy, for transmission out of the body, said image display ready signal adapted to be viewed on an image display; said CMOS image sensor being carried on said first endoscope branch;
    b) an objective lens carried on said first endoscope branch distal end on an optical axis and focusing an image corresponding to a first endoscope branch field of view at an image plane intersecting said optical axis; said CMOS image sensor pixels being disposed in said image plane and on said optical axis.

7. A method for viewing an endoscopic operation within the body, comprising:

introducing a branched endoscope having a first branch and a second branch into a body cavity, each of the first and second branches having a steerable distal end, respective ones of the steerable distal ends being independently steerable relative to one another;

steering the steerable distal end of the first endoscope branch into proximity with a site for surgery;

steering the steerable distal end of the second endoscope branch into a viewing orientation permitting visibility of the steerable distal end of the first endoscope branch.

8. A method for viewing an endoscopic operation within the body, comprising:

introducing a branched endoscope having a first branch and a second branch into a body cavity, each of the first and second branches having a steerable distal end, respective ones of the steerable distal ends being independently steerable relative to one another;

steering the steerable distal end of the first endoscope branch into proximity with a site for surgery providing visibility of the site for surgery from a first perspective; and steering the steerable distal end of the second endoscope branch into a viewing orientation permitting visibility of the site for surgery from a second perspective.

9. A branched endoscope system for providing a view of the surgical cavity, comprising:

an endoscope branch steering control mechanism;

a first endoscope branch having a steerable distal end and including a first image receiver generating a first image signal, said steerable distal end of said first endoscope branch being responsive to said endoscope branch steering control mechanism by moving to a desired orientation; and a second endoscope branch having a steerable distal end and including a second image receiver generating a second image signal whereby the first and second endoscope branches are sized and adapted for insertion into the surgical cavity through a single portal and are independently steerable relative to one another by the endoscope branch steering control mechanism.

10. The branched endoscope system of claim 9, wherein said second endoscope branch comprises a rigid tubular body.

11. The branched endoscope system of claim 9, wherein said second endoscope branch comprises a flexible tubular body.

12. The branched endoscope system of claim 9, wherein said first image receiver comprises a substantially planar complementary metal oxide semiconductor (CMOS) image sensor including a plurality of pixels and a pixel signal processing circuit generating an image ready signal, converting image light energy into electrical image display ready signal energy, for transmission out of the body, said image display ready signal adapted to be viewed on an image display; said CMOS image sensor being carried on said first endoscope branch distal end.

13. The branched endoscope system of claim 12, further comprising an objective lens carried on said first endoscope branch distal end on an optical axis and focusing an image corresponding to a first endoscope branch field of view at an image plane intersecting said optical axis; said CMOS image sensor pixels being disposed in said image plane and on said optical axis.

14. The branched endoscope system of claim 13, further including a color filter disposed along said optical axis proximate said image plane.

15. The branched endoscope system of claim 9 wherein said first endoscope branch further includes a light source.

16. The endoscope of claim 9 wherein said first endoscope branch further includes a cannula.

* * * * *